US010905381B2

(12) United States Patent
Yamashita et al.

(10) Patent No.: US 10,905,381 B2
(45) Date of Patent: Feb. 2, 2021

(54) BLOOD PRESSURE CORRECTION INFORMATION GENERATING DEVICE, BLOOD PRESSURE MEASUREMENT DEVICE AND BLOOD PRESSURE CORRECTION INFORMATION GENERATING METHOD

(71) Applicant: OMRON HEALTHCARE CO., LTD., Muko (JP)

(72) Inventors: Shingo Yamashita, Muko (JP); Kentaro Mori, Muko (JP); Yuki Ota, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 287 days.

(21) Appl. No.: 16/021,187

(22) Filed: Jun. 28, 2018

(65) Prior Publication Data
US 2018/0303428 A1  Oct. 25, 2018

Related U.S. Application Data (63) Continuation of application No. PCT/JP2016/083265, filed on Nov. 9, 2016.

(30) Foreign Application Priority Data

Jan. 4, 2016  (JP) .................................. 2016-000170

(51) Int. Cl.
*A61B 5/11*  (2006.01)
*A61B 5/02*  (2006.01)
(Continued)

(52) U.S. Cl.
CPC ................ *A61B 5/721* (2013.01); *A61B 5/02* (2013.01); *A61B 5/022* (2013.01);
(Continued)

(58) Field of Classification Search
CPC .......... A61B 5/02; A61B 5/021–02125; A61B 5/022–0235; A61B 5/11; A61B 5/1114;
(Continued)

(56) References Cited

U.S. PATENT DOCUMENTS

2004/0077958 A1  4/2004  Kato et al.
2011/0118613 A1*  5/2011  Yokoyama ............. A61B 5/022
600/486
(Continued)

FOREIGN PATENT DOCUMENTS

JP  H04-161143 A  6/1992
JP  2000-116609 A  4/2000
(Continued)

OTHER PUBLICATIONS

Jan. 10, 2017 International Search Report issued in International Patent Application No. PCT/JP2016/083265.
(Continued)

*Primary Examiner* — Thaddeus B Cox
(74) *Attorney, Agent, or Firm* — Oliff PLC (57) ABSTRACT

A blood pressure correction information generating device includes: a wrist position change time period detecting section which detects a change time period when a position of a wrist of a person is changed at a degree equal to or greater than a threshold based on information according to a motion of the wrist of the person to whom a blood pressure measurement device is attached, the blood pressure measurement device including a pulse wave detecting section which detects a pulse wave, and a blood pressure information calculating section which calculates blood pressure information; and a blood pressure correction information generating section which generates blood pressure correction information for correcting the blood pressure information which is calculated after the change time period, based
(Continued)

on first blood pressure information which is calculated before the change time period, and second blood pressure information which is calculated after the change time period.

8 Claims, 7 Drawing Sheets

(51) Int. Cl.
  *A61B 5/022* (2006.01)
  *A61B 5/021* (2006.01)
  *A61B 5/00* (2006.01)
(52) U.S. Cl.
  CPC ............ *A61B 5/02125* (2013.01); *A61B 5/11* (2013.01); *A61B 5/1114* (2013.01); *A61B 2562/0219* (2013.01)
(58) Field of Classification Search
  CPC ....... A61B 5/1116; A61B 5/1121–1122; A61B 5/7207–721
  See application file for complete search history.

(56) References Cited

U.S. PATENT DOCUMENTS

| | | | |
|---|---|---|---|
| 2011/0301476 A1 | 12/2011 | Sawanoi et al. | |
| 2015/0164437 A1* | 6/2015 | McCombie | A61B 5/1114 600/301 |
| 2015/0182147 A1* | 7/2015 | Sato | A61B 5/1079 600/493 |
| 2015/0327785 A1 | 11/2015 | Lading et al. | |
| 2015/0327786 A1* | 11/2015 | Lading | A61B 5/1126 600/437 |
| 2016/0029904 A1* | 2/2016 | Quinn | A61B 5/0024 600/499 |
| 2016/0198977 A1* | 7/2016 | Eom | A61B 5/02416 600/384 |
| 2017/0065184 A1* | 3/2017 | Barak | A61B 5/0507 |

FOREIGN PATENT DOCUMENTS

| | | |
|---|---|---|
| JP | 2004-113368 A | 4/2004 |
| JP | 2006-102190 A | 4/2006 |
| JP | 2010-194110 A | 9/2010 |
| JP | 2013-123529 A | 6/2013 |
| JP | 2014-068825 A | 4/2014 |
| WO | 02/039893 A1 | 5/2002 |
| WO | 2012/018029 A1 | 2/2012 |

OTHER PUBLICATIONS

Nov. 22, 2017 International Preliminary Report on Patentability issued in International Patent Application No. PCT/JP2016/083265.
Jul. 25, 2019 Extended Search Report issued in European Patent Application No. 16883687.2.

\* cited by examiner

BLOOD PRESSURE CORRECTION INFORMATION GENERATING DEVICE, BLOOD PRESSURE MEASUREMENT DEVICE AND BLOOD PRESSURE CORRECTION INFORMATION GENERATING METHOD

CROSS-REFERENCE TO RELATED APPLICATION(S)

This application is a continuation of PCT application No. PCT/JP2016/083265, which was filed on Nov. 9, 2016 based on Japanese Patent Application (No. 2016-000170) filed on Jan. 4, 2016, the contents of which are incorporated herein by reference.

BACKGROUND

1. Technical Field

The present invention relates to a blood pressure correction information generating device, a blood pressure measurement device, and a blood pressure correction information generating method.

2. Background Art

Usually, the blood pressure value of a living body shows a large diurnal change. In order to perform diagnosis or the like, therefore, a blood pressure measurement device is attached to a person to be measured, and blood pressure information is measured and recorded periodically (for example, at several hour intervals, or every pulse).

As a device suitable for consecutively measuring blood pressure information, a blood pressure measurement device is known that, in a state where a pressure sensor is directly contacted with a living body portion through which the radial artery in the wrist passes, can continuously (every pulse) measure blood pressure information by using information of a pressure pulse wave detected by the pressure sensor (see JP-A-2004-113368).

In a blood pressure measurement device which is to be used while attached to the wrist of a person to be measured, when blood pressure information is measured in a state where the wrist of the person to be measured, and the heart are at the same level, it is possible to obtain correct blood pressure information. Therefore, an acceleration sensor or the like is mounted on a blood pressure measurement device, the height difference between the wrist of the person to be measured and the heart is detected, and measured blood pressure information is corrected in accordance with the detected difference.

JP-A-04-161143 discloses a device in which information of an acceleration sensor attached to a living body, and blood pressure information are recorded in association with each other, and, from the recorded information, the correlation between the quantity of motion and a physiological change can be known in detail to be used in diagnosis.

In a blood pressure measurement device which is to be used while attached to the wrist of a person to be measured, in the case where the height difference between the heart of the person to be measured and the wrist is detected, there is a possibility that a detection error occurs. When a detection error is caused in the height difference between the wrist and the heart, an error in blood pressure information due to the hydrostatic pressure cannot be correctly corrected, and the blood pressure cannot be accurately measured.

In the device disclosed in JP-A-2004-113368, correction of the blood pressure information is not considered.

In the device disclosed in JP-A-04-161143, the degree of the daily life physical activity of a person to be measured is recorded together with the blood pressure information of the person. However, correction of an error in the blood pressure information caused by the height difference between the heart of the person to be measured and the wrist is not considered.

The invention has been conducted in view of the above circumstances. It is an object of the invention to provide a blood pressure correction information generating device that generates information with which a measurement error in blood pressure information that is caused by a position change of the wrist in a wrist-wear blood pressure measurement device can be correctly corrected, a blood pressure measurement device including the blood pressure correction information generating device, and a blood pressure correction information generating method.

SUMMARY

The blood pressure correction information generating device of the present invention includes: a wrist position change time period detecting section which detects a change time period when a position in a gravity direction of a wrist of a person to be measured is changed at a degree equal to or greater than a threshold, based on information that is output from a motion detecting section, the information according to a motion of the wrist of the person to be measured to whom a blood pressure measurement device is attached, the blood pressure measurement device including: a pulse wave detecting section which detects a pulse wave from the wrist of the person to be measured; and a blood pressure information calculating section which calculates blood pressure information every pulse or every plurality of pulses based on the pulse wave detected by the pulse wave detecting section; and a blood pressure correction information generating section which generates blood pressure correction information for correcting the blood pressure information which is calculated by the blood pressure information calculating section after the change time period detected by the wrist position change time period detecting section, based on first blood pressure information which is calculated by the blood pressure information calculating section before the change time period, and second blood pressure information which is calculated by the blood pressure information calculating section after the change time period.

The blood pressure measurement device of the present invention includes: a pulse wave detecting section which detects a pulse wave from a wrist of a person to be measured; a blood pressure information calculating section which calculates blood pressure information every pulse or every plurality of pulses based on the pulse wave detected by the pulse wave detecting section; a motion detecting section which outputs motion information according to motion of the wrist; and the blood pressure correction information generating device.

The blood pressure correction information generating method of the present invention includes: a wrist position change time period detecting step of detecting a change time period when a position in a gravity direction of a wrist of a person to be measured is changed at a degree equal to or greater than a threshold, based on information that is output from a motion detecting section, the information according to a motion of the wrist of the person to be measured to whom a blood pressure measurement device is attached, the blood pressure measurement device including: a pulse wave detecting section which detects a pulse wave from the wrist of the person to be measured; and a blood pressure information calculating section which calculates blood pressure information every pulse or every plurality of pulses based on the pulse wave detected by the pulse wave detecting section; and a blood pressure correction information generating step of generating blood pressure correction information for correcting the blood pressure information which is calculated by the blood pressure information calculating section after the change time period detected in the wrist position change time period detecting step, based on first blood pressure information which is calculated in the blood pressure information calculating section before the change time period, and second blood pressure information which is calculated by the blood pressure information calculating section, and which is after the change time period.

DESCRIPTION OF EXEMPLARY EMBODIMENTS

Hereinafter, an embodiment of the invention will be described with reference to the drawings.

Figure 1:
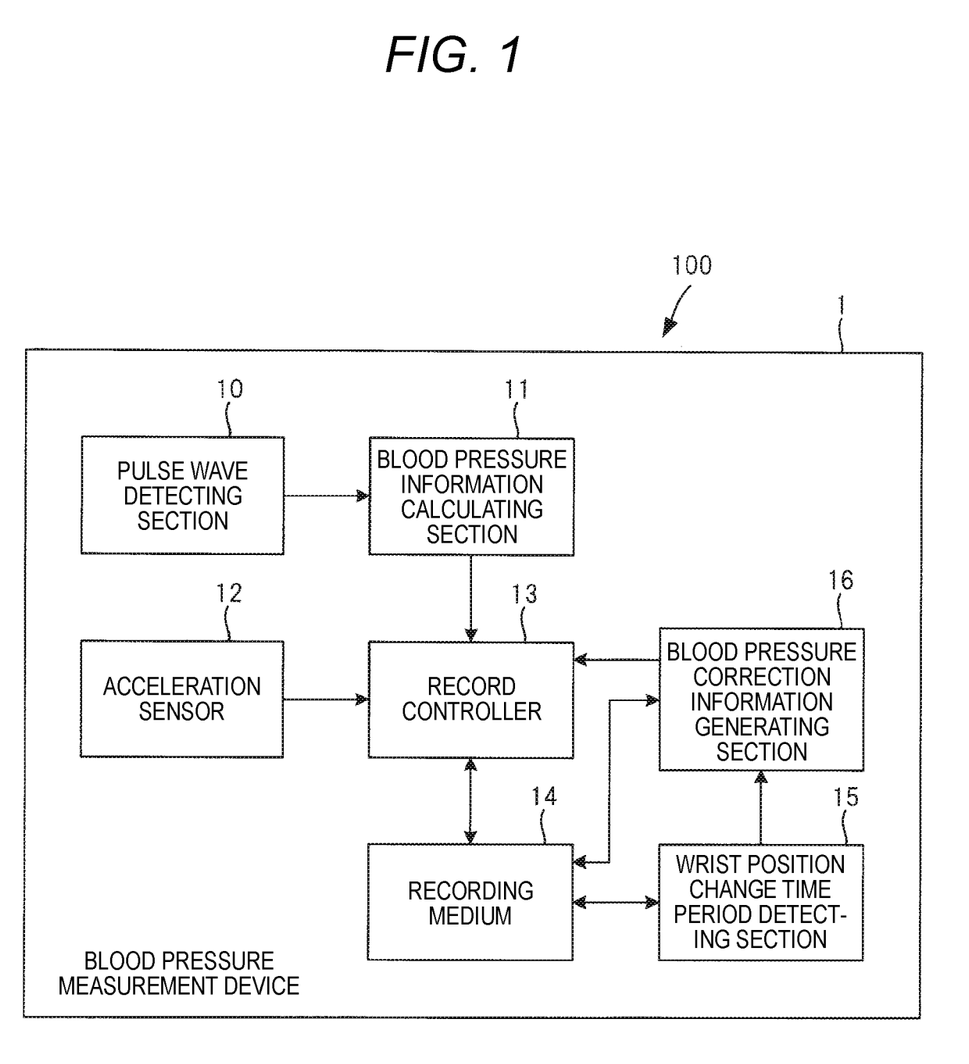
FIG. 1 is a diagram schematically showing the configuration of a blood pressure measurement device 100 for illustrating an embodiment of the invention.

FIG. 1 is a diagram schematically showing the configuration of a blood pressure measurement device 100 for illustrating an embodiment of the invention. The blood pressure measurement device 100 is of the portable type, and used while attached to the wrist of a person to be measured who functions as the living body.

The blood pressure measurement device 100 includes a pulse wave detecting section 10, a blood pressure information calculating section 11, an acceleration sensor 12, a record controller 13, a recording medium 14 such as a flash memory, a ROM (Read Only Memory), or a memory card, a wrist position change time period detecting section 15, and a blood pressure correction information generating section 16. The recording medium 14 may be detachable from the device.

The blood pressure information calculating section 11, the record controller 13, the wrist position change time period detecting section 15, and the blood pressure correction information generating section 16 are functional blocks which are formed by execution of programs by a processor.

The pulse wave detecting section 10 noninvasively detects a pulse wave from the wrist of the person to be measured. In the pulse wave detecting section 10, a configuration which detects a pressure pulse wave as the pulse wave by, for example, the tonometry method is used. Alternatively, the pulse wave detecting section 10 may detect a volume pulse wave as the pulse wave. The pulse wave detecting section 10 may detect the pulse wave from reflected light from the artery which is obtained by irradiating the artery with a light beam.

The pulse wave detecting section 10 detects a pulse wave which is generated every pulse (the time period when the heart pulsates one time), and transmits the detected pulse wave to the blood pressure information calculating section 11.

The blood pressure information calculating section 11 calculates blood pressure information in units of one pulse based on the pulse wave detected by the pulse wave detecting section 10. The calculation of blood pressure information in units of one pulse means that blood pressure information is calculated at each pulse, or that blood pressure information is calculated once every plurality of pulse (for example, every other pulse).

The blood pressure information contains the systolic blood pressure (SBP), the diastolic blood pressure (DBP), and the mean blood pressure (MBP).

In the method of calculating the blood pressure information, a known technique can be used. The blood pressure information calculating section 11 associates detection time information indicating the time of the detection time period of an arbitrary pulse wave with blood pressure information which is calculated based on the pulse wave, and transmits the resulting set of information to the record controller 13.

The acceleration sensor 12 is a motion detecting section which directly detects a motion of the wrist of the person to be measured, and which outputs information according to the motion.

In the embodiment, a three-axis acceleration sensor is used as the acceleration sensor 12. Three-axis acceleration information which is detected by the acceleration sensor 12 is transmitted to the record controller 13. The motion detecting section is requested to have a configuration which can detect a position change of the wrist in the gravity direction. For example, an angular velocity sensor, an atmospheric pressure sensor, or a geomagnetic sensor may be used, or two or more of these sensors may be combined with each other.

The record controller 13 records the set of the pulse wave detection time information and blood pressure information which are transmitted from the blood pressure information calculating section 11, on the recording medium 14.

The record controller 13 further records the acceleration information which is transmitted from the acceleration sensor 12, on the recording medium 14 while associating with the detection time of the information.

Under the control of the record controller 13, the blood pressure information (the SBP, the DBP, the MBP) which is calculated by the blood pressure information calculating section 11, the pulse wave detection time information based on which the blood pressure information is calculated, and the wrist motion information (three-axis acceleration information) that is detected by the acceleration sensor 12 during the detection time period of the pulse wave based on which the blood pressure information is calculated are recorded on the recording medium 14 while associated with one another.

Hereinafter, the detection time information which is recorded while associated with the motion information is referred to as the motion information detection time, and that which is recorded while associated with blood pressure information is referred to as the blood pressure information detection time.

The wrist position change time period detecting section 15 detects a change time period when the wrist position in the gravity direction is changed at a degree equal to or greater than a threshold, based on the wrist motion information recorded on the recording medium 14.

In the blood pressure measurement device 100, it is premised that the measurement of blood pressure information is started by pressing a measurement start button in a state where the position in the gravity direction of the wrist to which the blood pressure measurement device 100 is attached is set to be substantially identical with a predetermined reference position in the gravity direction (for example, the position in the gravity direction of the heart of the person to be measured).

With respect to the motion information which is recorded on the recording medium 14 after pressing of the measurement start button, for example, the wrist position change time period detecting section 15 subtracts from the position in the gravity direction based on each motion information, the position in the gravity direction corresponding to the time immediately before the detection time of the each motion information, thereby calculating a position difference between adjacent times, and records the calculated position difference between adjacent times while associating with the detection time of the each motion information.

Then, the wrist position change time period detecting section 15 checks the position differences between adjacent times in chronological order of the corresponding detection times, and, if the signs of position differences between adjacent times are identical with each other continuously a predetermined number of (a plurality of) times, determines that the wrist position in the gravity direction of the person to be measure is changed at a degree equal to or greater than the threshold.

The above-described determination method is an example. Any method in which a state where the position based on the motion information is largely increased or decreased can be determined may be employed.

Figure 2:
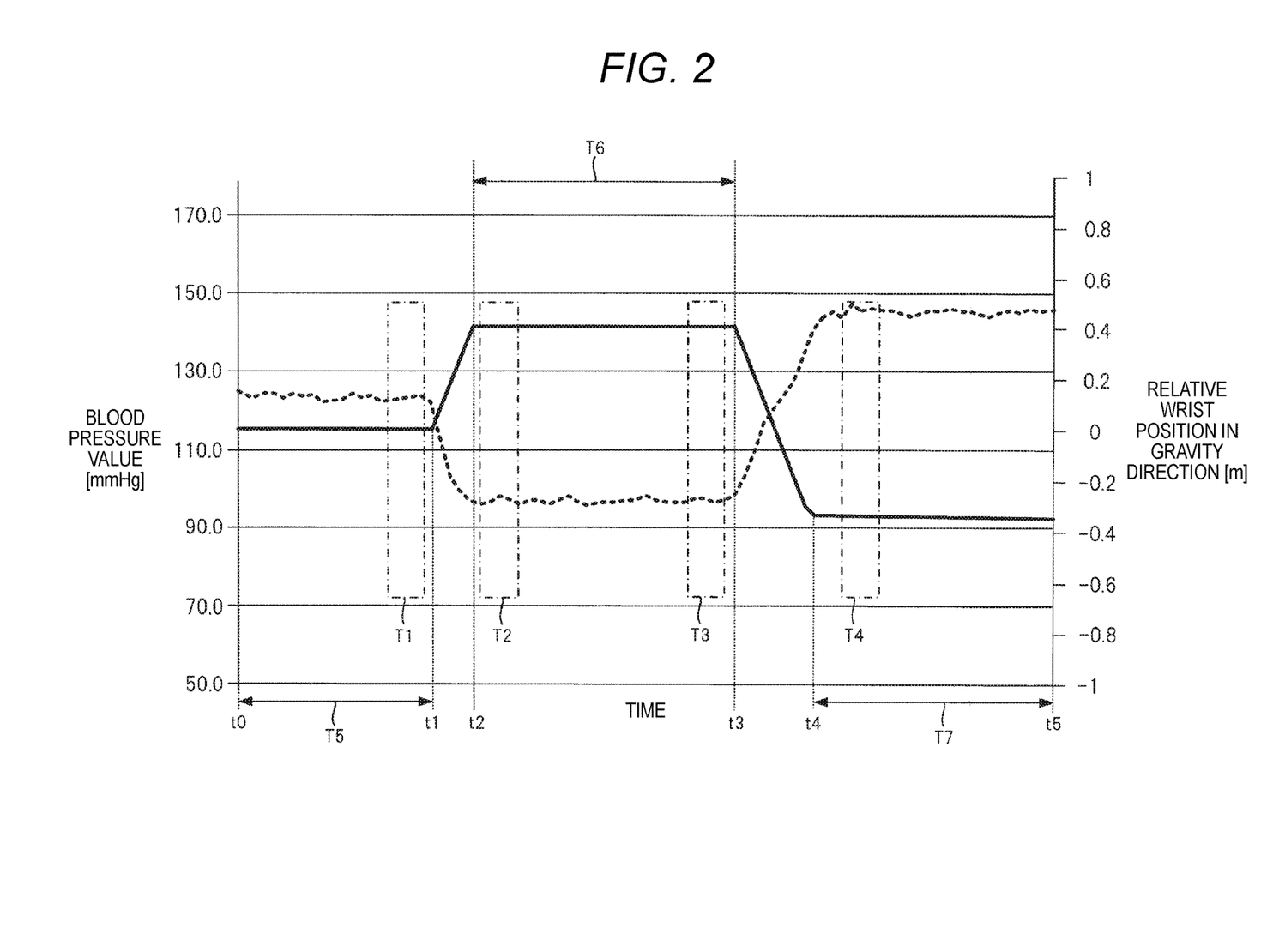
FIG. 2 is a view showing an example of blood pressure information measured by the blood pressure measurement device 100 shown in FIG. 1, and a wrist position change based on motion information during the measurement of the blood pressure information.

FIG. 2 is a view showing an example of blood pressure information measured by the blood pressure measurement device 100 shown in FIG. 1, and the wrist position change based on the motion information during the measurement of the blood pressure information. In FIG. 2, the blood pressure information is exemplified by the SBP, and indicated by the broken line.

In FIG. 2, moreover, the wrist position at the timing when the positions in the gravity direction of the wrist and the heart are substantially identical with each other is set as the reference position=0, and a change of the relative wrist position with respect to the reference position is indicated by the solid line.

In the example of FIG. 2, on or after time t1, the relative wrist position is continuously increased, and, while beginning at the time next to time t1, the signs of the position differences between adjacent times are plus continuously a predetermined number of times.

If, on or after the time next to time t1, the signs of the position differences between adjacent times are plus continuously a predetermined number of times, the wrist position change time period detecting section 15 determines that the wrist position is changed at a degree equal to or greater than the threshold.

The wrist position change time period detecting section 15 determines time t2 when, after, on or after the time next to time t1, the signs of the position differences between adjacent times are plus continuously a predetermined number of times, the position difference between adjacent times then becomes a minus value or zero, and detects the time period between the time next to time t1 and the time immediately before time t2, as the change time period when the wrist position is changed at a degree equal to or greater than the threshold.

In the example of FIG. 2, on or after time t3 after time t2, the relative wrist position is continuously decreased, and, while beginning at the time next to time t3, the signs of the position differences between adjacent times are minus continuously a predetermined number of times.

If, on or after the time next to time t3, the signs of the position differences between adjacent times are minus continuously a predetermined number of times, therefore, the wrist position change time period detecting section 15 determines that the wrist position is changed at a degree equal to or greater than the threshold.

The wrist position change time period detecting section 15 determines time t4 when, after, on or after the time next to time t3, the signs of the position differences between adjacent times are minus continuously a predetermined number of times, the position difference between adjacent times then becomes a plus value or zero, and detects the time period between the time next to time t3 and the time immediately before time t4, as the change time period when the wrist position is changed at a degree equal to or greater than the threshold.

When the change time period is detected by the wrist position change time period detecting section 15, the blood pressure correction information generating section 16 generates blood pressure correction information for correcting the blood pressure information which is calculated by the blood pressure information calculating section 11 after the detected change time period, based on first blood pressure information which is calculated by the blood pressure information calculating section 11 before the change time period, and second blood pressure information which is calculated by the blood pressure information calculating section 11 after the change time period.

The first blood pressure information and the second blood pressure information are the same kind of information. Namely, each of the first blood pressure information and the second blood pressure information is any one of the SBP, the DBP, and the MBP.

The term "correction" in the specification means correction of a measured error in blood pressure information which is generated due to the difference between the position in the gravity direction of the wrist to which the blood pressure measurement device 100 is attached, and the position of the heart of the person to be measured, the position of the heart being the reference position.

The blood pressure correction information generating section 16 selects by a first time period before the change time period detected by the wrist position change time period detecting section 15, and calculates the typical value of the first blood pressure information which is calculated by the blood pressure information calculating section 11 during the first time period.

The blood pressure correction information generating section 16 further selects a second time period after the change time period, and calculates the typical value of the second blood pressure information which is calculated by the blood pressure information calculating section 11 during the second time period. The blood pressure correction information generating section 16 generates blood pressure correction information based on the differential between the two typical values.

The blood pressure information which is calculated by the blood pressure information calculating section 11 during a certain time period mans blood pressure information to which times contained in the time period are associated as detection times.

Moreover, the typical value of blood pressure information which is calculated by the blood pressure information calculating section 11 during a certain time period mans a value indicating the outline of a plurality of sets of blood pressure information which are calculated during the time period, such as the mean value of a plurality of sets of blood pressure information which are calculated during the time period, the mode of the plurality of sets of blood pressure information, or the mean value of sets of blood pressure information which are remaining sets of blood pressure information that are obtained by removing the maximum and minimum values from the sets of blood pressure information.

The blood pressure correction information generating section 16 selects, as the first and second time periods, a time period that is closest to the change time period, among time periods during which dispersion of blood pressure information calculated by the blood pressure information calculating section 11 is equal to or smaller than a variation threshold.

In the example of FIG. 2, the blood pressure correction information generating section 16 sets a first window which begins at time t1 that is immediately before the starting time of the change time period, and which extends toward a time older than time t1, and which has a width of a predetermined time period, and calculates the standard deviation of blood pressure information with which times in the set first window are associated.

While sequentially shifting the first window in the step of the minimum unit time in the direction in which the time travels back, the blood pressure correction information generating section 16 calculates the standard deviation at the positions where the first windows are set. The standard deviation indicates dispersion of blood pressure information in the set first window.

The blood pressure correction information generating section 16 determines whether the standard deviation calculated by using the first window is equal to or smaller than the above-described variation threshold or not, and selects the time period during which the first window from which the standard deviation that is equal to or smaller than the variation threshold is obtained at the first time is set, as the first time period.

In the example of FIG. 2, the blood pressure correction information generating section 16 selects a time period T1 during which the standard deviation is equal to or smaller than the variation threshold at the first time on or before time t1. Similarly, the blood pressure correction information generating section 16 selects a time period T3 during which the standard deviation is equal to or smaller than the variation threshold at the first time on or before time t3 that is immediately before the starting time of the change time period, as the first time period.

Similarly, the blood pressure correction information generating section 16 sets a second window which begins at time t2 that is next to the time when the change time period ends, which extends toward a time newer than time t2, and which has the same width as the first window, and calculates the standard deviation of blood pressure information with which times in the set second window are associated. While sequentially shifting the second window in the step of the minimum unit time in the direction in which the time travels, the blood pressure correction information generating section 16 calculates the standard deviation at the positions where the second windows are set.

The blood pressure correction information generating section 16 determines whether the standard deviation calculated by using the second window is equal to or smaller than the above-described variation threshold or not, and selects the time period during which the second window from which the standard deviation that is equal to or smaller than the variation threshold is obtained at the first time is set, as the second time period.

In the example of FIG. 2, the blood pressure correction information generating section 16 selects a time period T2 during which the standard deviation is equal to or smaller than the variation threshold at the first time on or after time t2, as the second time period. Similarly, the blood pressure correction information generating section 16 selects a time period T4 during which the standard deviation is equal to or smaller than the variation threshold at the first time on or after time t4 that is immediately after the ending time of the change time period, as the second time period.

The differential between the typical value of blood pressure information which is calculated during the first time period (time period T1 in FIG. 2) that is selected in this way, and that of blood pressure information which is calculated during the second time period (time period T2 in FIG. 2) is a change amount of blood pressure information which is caused by a change of the wrist position that is equal to or larger than the threshold, and corresponds to a measurement error in blood pressure information that is caused by motion of the wrist.

When the differential is used, therefore, blood pressure correction information for correcting the measurement error can be generated.

The record controller 13 records the blood pressure correction information which is generated by the blood pressure correction information generating section 16 based on the blood pressure information in the first and second time periods that are before and after an arbitrary change time period, on the recording medium 14 while associating with blood pressure information (blood pressure information corresponding to a time after the change time period) which is calculated by the blood pressure information calculating section 11 after the change time period.

In the example of FIG. 2, the blood pressure correction information which is generated based on the differential between the typical value of the blood pressure information in the time period T1 and that of the blood pressure information in the time period T2 is recorded while associated with the blood pressure information (the SBP, the DBP, and the MBP) on or after time t2.

The blood pressure correction information which is generated based on the differential between the typical value of the blood pressure information in the time period T3 and that of the blood pressure information in the time period T4 is recorded while associated with the blood pressure information (the SBP, the DBP, and the MBP) on or after time t4.

With respect to the blood pressure information (the SBP, the DBP, and the MBP) corresponding to times during the change time period detected by the wrist position change time period detecting section 15, the record controller 13 records information indicating that it is during the change time period, and the blood pressure correction information while associating with the information.

With respect to the blood pressure information (the SBP, the DBP, and the MBP) corresponding to times during the change time, the record controller 13 may record only information indicating that it is during the change time period while associating with the information.

The record controller 13 records the blood pressure information (the SBP, the DBP, and the MBP) corresponding to times during the time period (in the example of FIG. 2, the time period between times t0 to t1) extending pressing of the measurement start button to first detection of the change time period, while associating with information of a correction value=0 as blood pressure correction information.

The operation of the thus configured blood pressure measurement device 100 will be described.

Figure 3:
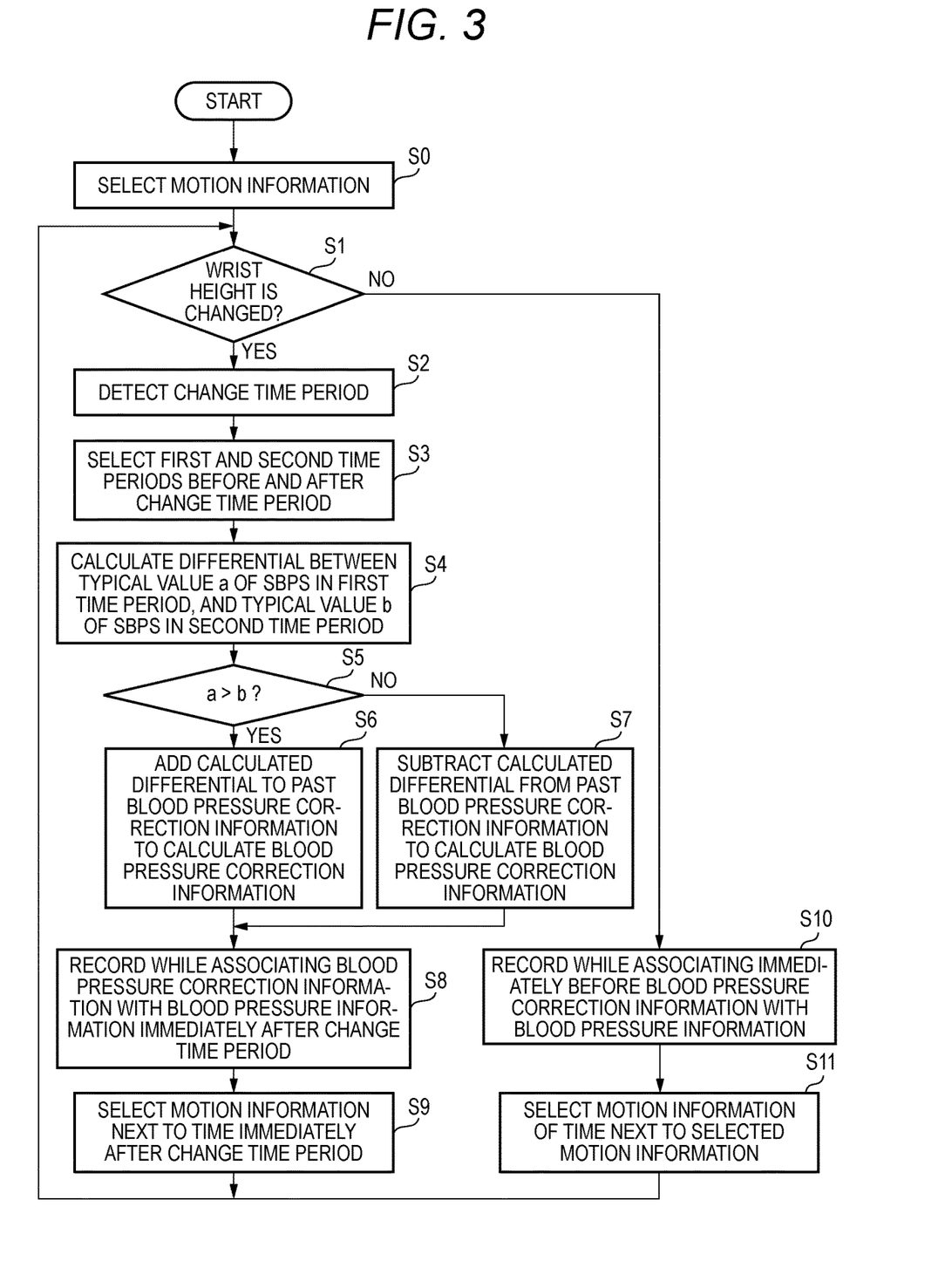
FIG. 3 is a flowchart illustrating the operation of the blood pressure measurement device 100 shown in FIG. 1, in generation of blood pressure correction information.

FIG. 3 is a flowchart illustrating the operation of the blood pressure measurement device 100 shown in FIG. 1, in generation of blood pressure correction information.

The person to be measured attaches the blood pressure measurement device 100 to the wrist, and presses the measurement start button in a state where the wrist position in the gravity direction is identical with the position of the heart, thereby instructing start of the measurement. In response to the instructions, the pulse wave detection by the pulse wave detecting section 10 is started, the motion information is output from the acceleration sensor 12, and the blood pressure information (the SBP, the DBP, and the MBP) which is calculated based on the pulse wave, and the motion information are recorded on the recording medium 14 while associated with the detection time information.

Among blood pressure information recorded on the recording medium 14, information in which the detection time is oldest is recorded while associated with blood pressure correction information in which the initial value=0 is set.

When the blood pressure information and motion information for a time period of a certain length are recorded on the recording medium 14, the wrist position change time period detecting section 15 selects information having the second oldest detection time from the motion information recorded on the recording medium 14 (step S0).

Next, the wrist position change time period detecting section 15 determines whether, at the detection time of the selected motion information, the wrist position in the gravity direction is changed at a degree equal to or greater than the threshold or not, based on the selected motion information and motion information corresponding to a time which is older than the detection time of the selected motion information (step S1).

If a change which is equal to or larger than the threshold does not occur in the wrist position in the gravity direction (step S1: NO), the record controller 13 performs recording while associating blood pressure information (each of the SBP, the DBP, and the MBP) corresponding to the detection time of the selected motion information, with past blood pressure correction information corresponding to the blood pressure information (the SBP, the DBP, and the MBP) corresponding to the time immediately before the detection time (step S10).

After step S10, the wrist position change time period detecting section 15 selects motion information corresponding to the time next to the detection time of the currently selected motion information (step S11), and returns the process to step S1.

If a change which is equal to or larger than the threshold occurs in the wrist position in the gravity direction (step S1: YES), the wrist position change time period detecting section 15 determines the time when the change ends based on the motion information which is detected after the currently selected motion information, and which is recorded on the recording medium 14, and detects the change time period (step S2).

Based on an arbitral kind of blood pressure information (hereinafter, assumed as the SBP) recorded on the recording medium 14, after step S2, the blood pressure correction information generating section 16 selects the first time period during which dispersion of the SBP is equal or smaller than the threshold before the detected change time period, and the second time period during which dispersion of the SBP is equal or smaller than the threshold after the detected change time period (step S3).

After step S3, the blood pressure correction information generating section 16 calculates the differential between the typical value (hereinafter, referred to as "a") of the SBPs corresponding to the times during the first time period selected in step S3, and the typical value (hereinafter, referred to as "b") of the SBPs corresponding to the times during the second time period selected in step S3 (step S4).

After step S4, the blood pressure correction information generating section 16 determines the magnitude relationship of the typical value a selected in step S3, and the typical value b selected in step S3 (step S5).

If the typical value a is larger than the typical value b (step S5: YES), the blood pressure correction information generating section 16 adds the absolute value of the differential calculated in step S4 to the past blood pressure correction information which is recorded while associated with the blood pressure information corresponding to the time immediately before the change time period detected in step S2, thereby calculating the blood pressure correction information (step S6).

If the typical value a is smaller than the typical value b (step S5: NO), the blood pressure correction information generating section 16 subtracts the absolute value of the differential calculated in step S4 from the past blood pressure correction information which is recorded while associated with the blood pressure information corresponding to the time immediately before the change time period detected in step S2, thereby calculating the blood pressure correction information (step S7).

After steps S6 and S7, the record controller 13 records the blood pressure correction information calculated in step S6 or S7 while associating with the blood pressure information corresponding to the time immediately after the change time period detected in step S2 (step S8).

After step S8, the wrist position change time period detecting section 15 selects the motion information corresponding to the time next to the time immediately after the change time period detected in step S2 (step S9), and returns the process to step S1. The above processes are repeated, and blood pressure correction information is therefore recorded while associated with all sets of blood pressure information excluding sets of blood pressure information corresponding to times in the change time period.

The processes of steps S6 to S8 will be specifically described with reference to FIG. 2.

In FIG. 2, it is assumed that the measurement is started at time t0. Therefore, the initial value "0" is recorded as blood pressure correction information while associated with the SBPs corresponding to the times of the periods T5 between times t0 to t1.

When the change time period between times t1 to t2 is detected, the differential between the typical values of the SBPs in the time periods T1, T2 before and after the change time period is calculated. In the example of FIG. 2, the absolute value of the differential is "23 mmHg."

In the SBPs corresponding to times in time period T6 between time t2 to time t3 immediately before the start of the next change time, therefore, an error of "−23 mmHg" occurs with respect to the correct value. In order to correct the error, the blood pressure correction information can be set to "+23 mmHg."

The blood pressure correction information corresponding to the SBPs corresponding to times in time period T5 is "0 mmHg." When "23 mmHg" which is the absolute value of the differential between the typical values of the SBPs in the time periods T1, T2 is added to "0 mmHg," therefore, the blood pressure correction information of "+23 mmHg" can be obtained. This adding process corresponds to step S6 of FIG. 3.

When the change time period between times t3 to t4 is detected in FIG. 2, the differential between the typical values of the SBPs in the time periods T3, T4 before and after the change time period is calculated. In the example of FIG. 2, the absolute value of the differential is "50 mmHg."

In the SBPs corresponding to times in time period T7 after time t4, therefore, an error of "+50 mmHg" occurs with respect to the SBPs in time period T6. In the SBPs in time period T6, as described above, an error of "−23 mmHg" originally occurs with respect to the correct value.

In the SBPs corresponding to times in time period T7, therefore, an error of 50−23=27 mmHg occurs with respect to the correct value. In order to correct the error, the blood pressure correction information can be set to "−27 mmHg."

The blood pressure correction information corresponding to the SBPs corresponding to times in time period T6 is "+23 mmHg." When "50 mmHg" which is the differential between the typical values of the SBPs in the time periods T3, T4 is subtracted from "+23 mmHg," therefore, the blood pressure correction information of "−27 mmHg" can be obtained. This subtracting process corresponds to step S7 of FIG. 3.

Based on the magnitude relationship of the typical value which is calculated from the SBPs during the first time period, and that which is calculated from the SBPs during the second time period, as described above, the absolute value of the differential between the two typical values is added to the past blood pressure correction information associated with the blood pressure information before the change time period, or the absolute value is subtracted from the past blood pressure correction information, whereby the correct blood pressure correction information can be calculated and recorded each time when the change time period is detected.

According to the blood pressure measurement device 100, as described above, a change time period when the wrist position of the person to be measured is largely changed can be detected, and the blood pressure correction information can be generated based on the change amount of the blood pressure information before and after the change time period.

The blood pressure measurement device 100 is requested only to determine whether the wrist position in the gravity direction is largely changed or not, and determine the start and end of the change. As the acceleration sensor 12, therefore, it is not required to use an expensive sensor in which the detection accuracy is high. Moreover, a complex process of correctly detecting the amount of the positional difference between the wrist and heart positions in the gravity direction is not necessary. Therefore, the production cost of the blood pressure measurement device 100 can be reduced. The correction is enabled without being affected by the detection error of the difference amount, and the blood pressure information can be correctly corrected.

Moreover, the blood pressure measurement device 100 generates the blood pressure correction information based on the differential between typical values of the SBPs during time periods (the first and second time periods) when the SBPs are less dispersed before and after the change time period. Therefore, the change amount of the blood pressure information due to a change of the wrist position can be extracted more correctly, and the reliability of the blood pressure correction information can be enhanced.

In the above description, the blood pressure information which is used for calculating the typical values in step S4 of FIG. 3 is the SBP. Alternatively, the DBP or the MBP may be used as the blood pressure information.

Hereinafter, modifications of the blood pressure measurement device 100 will be described.

(First Modification)

Figure 4:
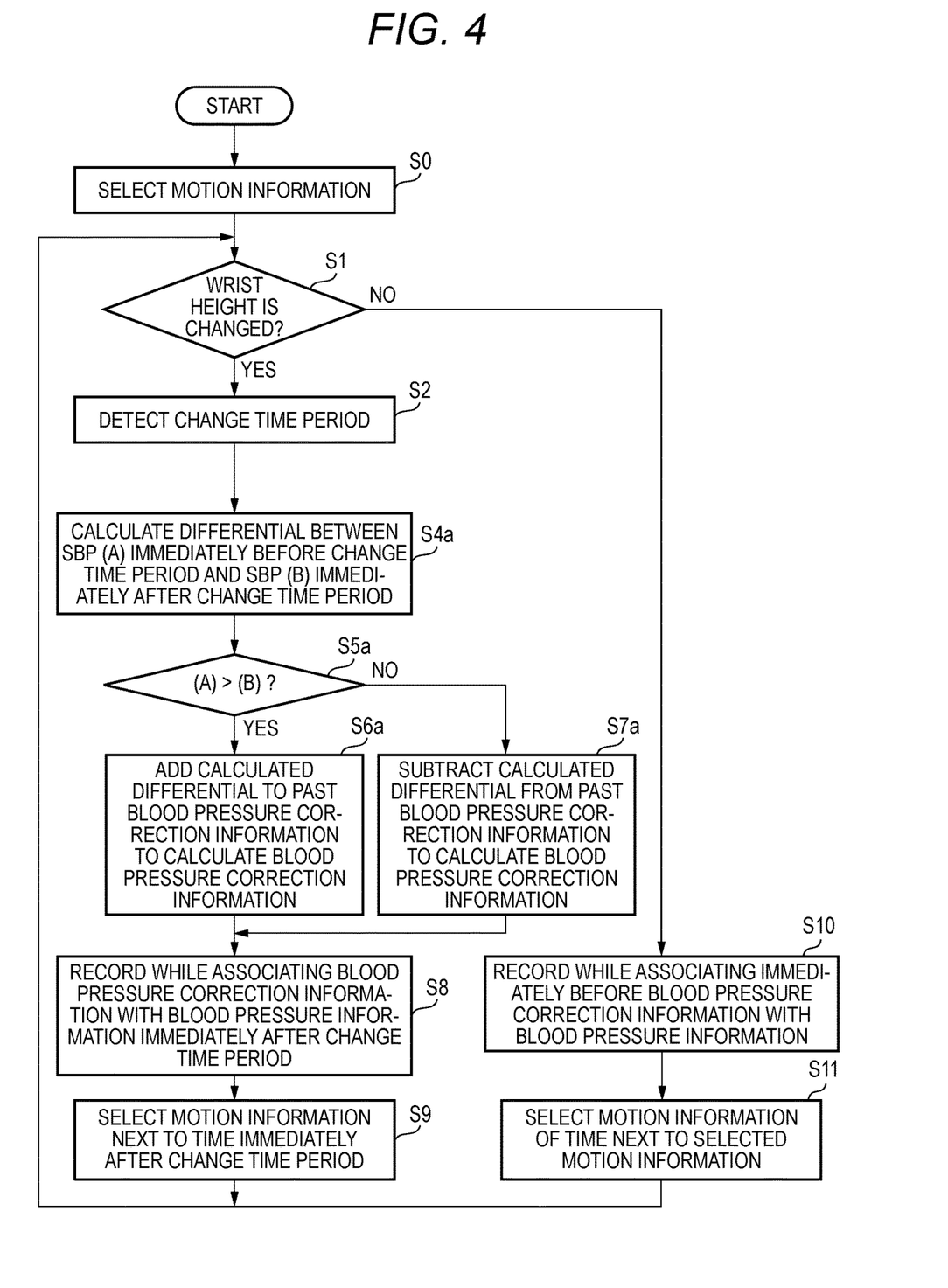
FIG. 4 is a flowchart illustrating a first modification of the operation of the blood pressure measurement device 100 shown in FIG. 1, in generation of blood pressure correction information.

FIG. 4 is a flowchart illustrating a first modification of the operation of the blood pressure measurement device 100 shown in FIG. 1, in generation of the blood pressure correction information. In FIG. 4, the processes identical with those of FIG. 3 are denoted by the same reference numerals, and their description is omitted.

The flowchart of FIG. 4 is identical with that of FIG. 3 except that step S3 is deleted, step S4 is changed to step S4a, step S5 is changed to step S5a, step S6 is changed to step S6a, and step S7 is changed to step S7a.

After step S2, the blood pressure correction information generating section 16 calculates the differential between the SBP (hereinafter, referred to as "(A)") corresponding to the time immediately before the change time period detected in step S2, and the SBP (hereinafter, referred to as "(B)") corresponding to the time immediately after the change time period detected in step S2 (step S4a).

Next, the blood pressure correction information generating section 16 determines the magnitude relationship of the SBP (A) calculated in step S4a, and the SBP (B) calculated in step S4a (step S5a).

If the SBP (A) is larger than the SBP (B) (step S5a: YES), the blood pressure correction information generating section 16 adds the absolute value of the differential calculated in step S4a to the past blood pressure correction information which is recorded while associated with the blood pressure information corresponding to the time immediately before the change time period detected in step S2, thereby calculating the blood pressure correction information (step S6a).

If the SBP (A) is smaller than the SBP (B) (step S5a: NO), the blood pressure correction information generating section 16 subtracts the absolute value of the differential calculated in step S4a from the past blood pressure correction information which is recorded while associated with the blood pressure information corresponding to the time immediately before the change time period detected in step S2, thereby calculating the blood pressure correction information (step S7a).

After steps S6a and S7a, the process of step S8 is performed.

According to the modification of FIG. 4, the process of determining the first and second time periods, and calculating the typical values can be omitted. Therefore, the amount of calculation for generating the blood pressure correction information can be reduced, and the power consumption of the blood pressure measurement device 100 can be reduced.

(Second Modification)

Figure 5:
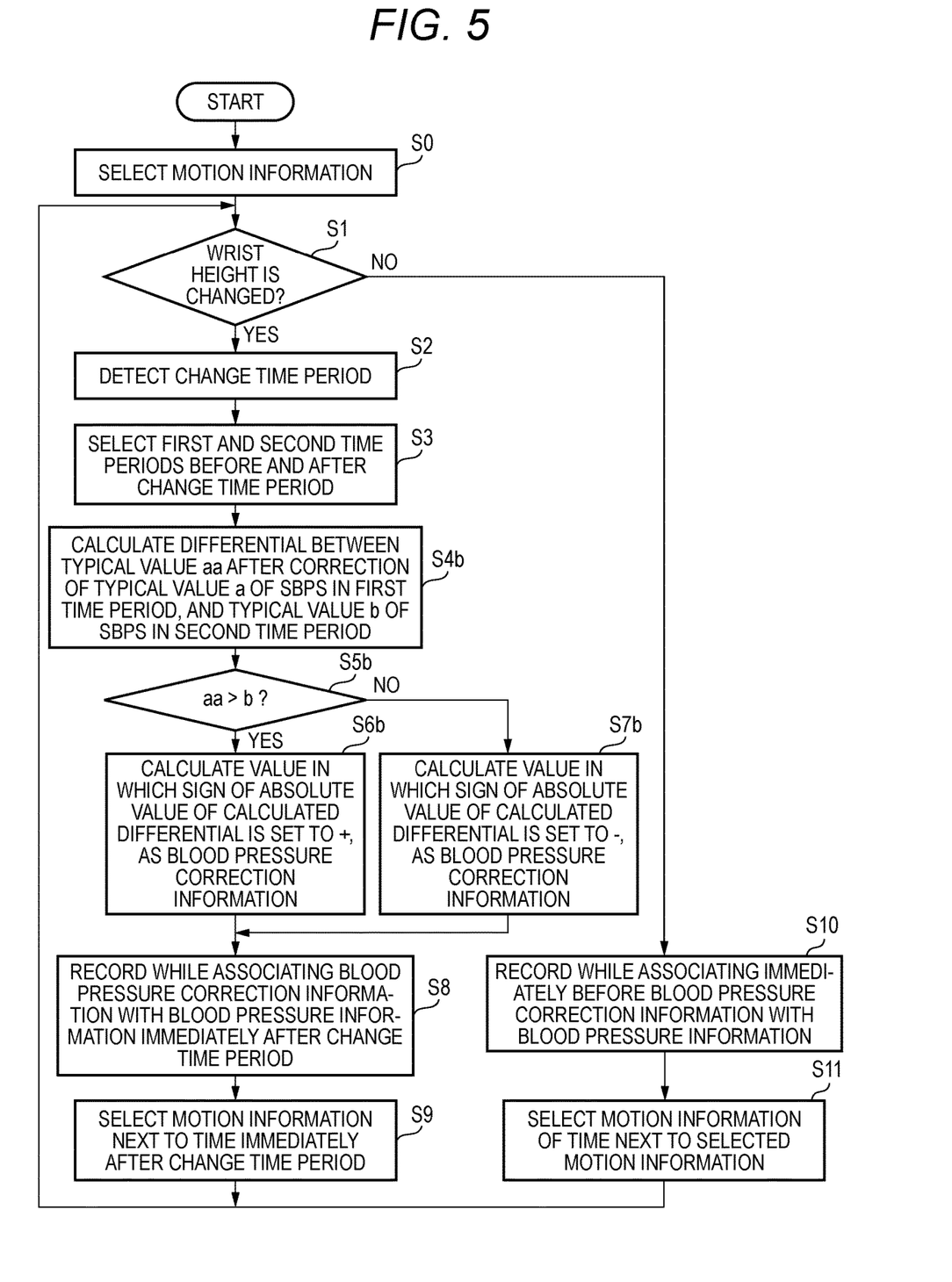
FIG. 5 is a flowchart illustrating a second modification of the operation of the blood pressure measurement device 100 shown in FIG. 1, in generation of blood pressure correction information.

FIG. 5 is a flowchart illustrating a second modification of the operation of the blood pressure measurement device 100 shown in FIG. 1, in generation of blood pressure correction information. In FIG. 5, the processes identical with those of FIG. 3 are denoted by the same reference numerals, and their description is omitted.

The flowchart of FIG. 5 is identical with that of FIG. 3 except that step S4 is changed to step S4b, step S5 is changed to step S5b, step S6 is changed to step S6b, and step S7 is changed to step S7b.

In step S4b, the blood pressure correction information generating section 16 corrects the typical value a of the SBPs corresponding to the times during the first time period selected in step S3, by the blood pressure correction information which is recorded while associated with the blood pressure information corresponding to the times during the first time period, thereby obtaining a typical value aa. Moreover, the blood pressure correction information generating section 16 calculates the typical value b of the SBPs corresponding to the times during the second time period selected in step S3. Then, the blood pressure correction information generating section 16 calculates the differential between the typical value aa and the typical value b.

After step S4b, the blood pressure correction information generating section 16 determines the magnitude relationship of the typical value aa and the typical value b (step S5b).

If the typical value aa is larger than the typical value b (step S5b: YES), the blood pressure correction information generating section 16 calculates a value in which the sign of the absolute value of the differential calculated in step S4b is set to plus, as the blood pressure correction information (step S6b).

If the typical value aa is smaller than the typical value b (step S5b: NO), the blood pressure correction information generating section 16 calculates a value in which the sign of the absolute value of the differential calculated in step S4b is set to minus, as the blood pressure correction information (step S7b).

After steps S6b and S7b, the process of step S8 is performed.

According to the modification of FIG. 5, similarly with the operation of FIG. 3, the blood pressure correction information can be accurately obtained at a low cost.

(Third Modification)

Figure 6:
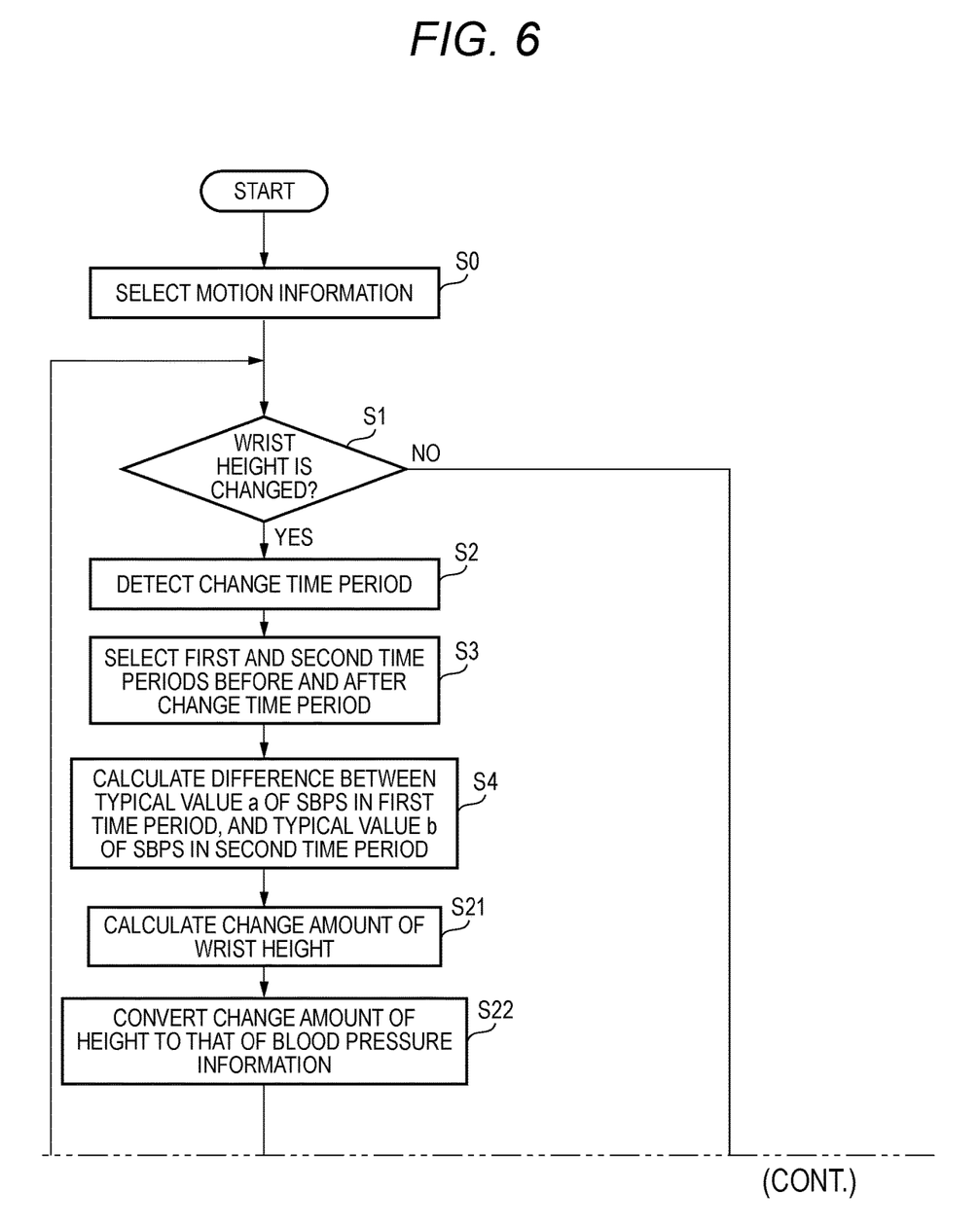
FIG. 6 is a flowchart illustrating a third modification of the operation of the blood pressure measurement device 100 shown in FIG. 1, in generation of blood pressure correction information.

FIG. 6 is a flowchart illustrating a third modification of the operation of the blood pressure measurement device 100 shown in FIG. 1, in generation of blood pressure correction information. In FIG. 6, the processes identical with those of FIG. 3 are denoted by the same reference numerals, and their description is omitted.

The flowchart of FIG. 6 is identical with that of FIG. 3 except that steps S21 to S23 are added.

After step S4, the blood pressure correction information generating section 16 calculates a change amount of the wrist height which is the difference between the wrist position due to the motion information at the start of the change time period that is detected in step S2, and the wrist position due to the motion information at the end of the change time period that is detected in step S2 (step S21).

After step S21, the blood pressure correction information generating section 16 obtains the change amount of the blood pressure information from the calculated height change amount by using a table indicating relationships of the wrist height change amount which is previously recorded in the blood pressure measurement device 100, and the change amount of the blood pressure information (step S22).

After step S22, the blood pressure correction information generating section 16 determines whether the difference between the change amount of the blood pressure information obtained in step S22, and the differential between the typical values a and b calculated in step S4 is larger than a predetermined value or not (step S23).

If the determination in step S23 is YES, the blood pressure correction information generating section 16 determines that the variation of the SBPs before and after the change time period is not caused by the wrist position change, and some kind of abnormality occurs, and ends the process of generating the blood pressure correction information.

In consideration that there is a possibility that an error is contained in the change amount of the wrist height which is calculated based on the motion information, the above-described predetermined value is set to a value that is large to some extent (for example, about 10 mmHg).

If the determination in step S23 is NO, the blood pressure correction information generating section 16 determines that the variation of the SBPs before and after the change time period is caused by the change of the wrist position, and performs the processes of step S5 and subsequent steps.

According to the modification, the case where the SBP is varied by a cause other than the wrist position change is determined, and, in the case, the generation of the blood pressure correction information is stopped, whereby the reliability of the blood pressure correction information recorded on the recording medium 14 can be enhanced. The third modification may be combined with the first modification or the second modification.

In the case of the combination with the first modification, step S21 and step S22 of FIG. 6 are added between step S2 and step S4a of FIG. 4, the difference between the differential calculated in step S4a and the change amount of the blood pressure information obtained in step S22 is obtained after step S4a, and, if the difference is larger than the predetermined value, the generation of the blood pressure correction information is stopped, and, if the difference is equal to or smaller than the predetermined value, the processes of step S5a and subsequent steps are performed.

In the case of the combination with the second modification, step S21 and step S22 of FIG. 6 are added between step S2 and step S3 of FIG. 5, the difference between the differential calculated in step S4b and the change amount of the blood pressure information obtained in step S22 is obtained after step S4b, and, if the difference is larger than the predetermined value, the generation of the blood pressure correction information is stopped, and, if the difference is equal to or smaller than the predetermined value, the processes of step S5b and subsequent steps are performed.

The blood pressure measurement device 100 may have a blood pressure correcting section which corrects the blood pressure information based on the blood pressure correction information generated by the blood pressure correction information generating section 16. The blood pressure correcting section is a functional block which is formed by execution of programs by the processor.

After the generation and recoding of blood pressure correction information are ended by the methods which have been described with reference to FIGS. 3 to 6, the blood pressure correcting section corrects the blood pressure information (each of the SBP, the DBP, and the MBP) which is recorded on the recording medium 14, by using the blood pressure correction information associated with the blood pressure information, and records the corrected blood pressure information on the recording medium 14.

With respect to blood pressure information associated with the information indicating that it is during the change time period, the blood pressure correcting section may not perform the correction, and may record the blood pressure information while associated with information indicating that the value is invalid, or delete the blood pressure information itself.

As shown in FIG. 2, the blood pressure information is largely varied during the change time period. Therefore, blood pressure information during the change time period is information which is not suitable for use in diagnosis. When blood pressure information during the change time period is made invalid or deleted, consequently, the blood pressure condition of the person to be measured can be correctly known from the blood pressure information recorded on the recording medium 14.

In the description of the operations of FIGS. 3 to 6, it is assumed that the blood pressure measurement and the generation and recording of blood pressure correction information are performed in parallel. However, the generation of blood pressure correction information may be performed after the blood pressure measurement is ended.

In the above description, it is assumed that the generation and recording of blood pressure correction information are performed in the blood pressure correction measurement device 100. The generation and recording of blood pressure information may be performed by another electronic device (a smart phone, a tablet terminal, a personal computer, or the like) which can communicate wiredly or wirelessly with the blood pressure measurement device 100.

In this case, the processor of the electronic device executes programs for causing a computer to function as the record controller 13, wrist position change time period detecting section 15, blood pressure correction information generating section 16, and blood pressure correcting section of the blood pressure measurement device 100, thereby performing the processes shown in FIGS. 3 to 6 based on the blood pressure information and motion information which are recorded on the recording medium 14 of the blood pressure measurement device 100.

Such programs may be recorded on a non-transitory computer readable recording medium, and then provided to a medical institution or the like. For example, such "computer readable recording medium" includes an optical medium such as a CD-ROM (Compact Disc-ROM), a magnetic recording medium such as a memory card, and the like.

Preferably, such programs can be downloaded via a network such as the Internet. In this configuration, a tablet terminal, smart phone, or personal computer which already exists in a medical institution can be easily used as the blood pressure correction information generating device, and the cost of introduction of the system into the medical institution can be suppressed.

In the above description, it is assumed that the DBP, the SBP, and the MBP are recorded as blood pressure information on the recording medium 14, and blood pressure correction information is recorded while associated with each of the DBP, the SBP, and the MBP. However, a configuration where at least one of the DBP, the SBP, and the MBP is recorded on the recording medium 14 may be possible.

It is known that, among the DBP, the SBP, and the MBP, the SBP is largely varied even in a state where the wrist position is not changed. Therefore, it is preferable to employ the DBP or the MBP as the blood pressure information (the blood pressure information which is used in step S3 for selecting the time period, that which is used in step S4 and step S4b for calculating the typical values, or that which is used in step S4a for calculating the differential) which is used for generating the blood pressure correction information.

In the blood pressure measurement device 100, in the case where blood pressure information is calculated and recorded for each of a plurality of pulses, it is preferable to decimate blood pressure information at a degree which can ensure to some extent the generation accuracy of the blood pressure correction information. Preferably, the degree is set so that one set of blood pressure information is recorded every two to ten pulses on the recording medium 14.

The presently disclosed embodiment should be considered in all respects to be illustrative and not restrictive. The scope of the invention is indicated by the appended claims rather than by the foregoing description, and all changes which come within the meaning and range of equivalents thereof are intended to be embraced therein.

As described above, the following matters are disclosed in the specification.

The disclosed blood pressure correction information generating device includes: a wrist position change time period detecting section which detects a change time period when a position in a gravity direction of a wrist of a person to be measured is changed at a degree equal to or greater than a threshold, based on information that is output from a motion detecting section, the information according to a motion of the wrist of the person to be measured to whom a blood pressure measurement device is attached, the blood pressure measurement device including: a pulse wave detecting section which detects a pulse wave from the wrist of the person to be measured; and a blood pressure information calculating section which calculates blood pressure information every pulse or every plurality of pulses based on the pulse wave detected by the pulse wave detecting section; and a blood pressure correction information generating section which generates blood pressure correction information for correcting the blood pressure information which is calculated by the blood pressure information calculating section after the change time period detected by the wrist position change time period detecting section, based on first blood pressure information which is calculated by the blood pressure information calculating section before the change time period, and second blood pressure information which is calculated by the blood pressure information calculating section after the change time period.

In the disclosed blood pressure correction information generating device, the blood pressure correction information generating section generates the blood pressure correction information based on a differential between a typical value of the first blood pressure information which is calculated by the blood pressure information calculating section during a first time period that is before the change time period, and a typical value of the second blood pressure information which is calculated by the blood pressure information calculating section during a second time period that is after the change time period, the first time period is a time period when dispersion of the blood pressure information calculated by the blood pressure information calculating section is equal to or smaller than a threshold, and the second time period is a time period when dispersion of the blood pressure information calculated by the blood pressure information calculating section is equal to or smaller than the threshold.

In the disclosed blood pressure correction information generating device, the blood pressure correction information generating section calculates the differential while setting a mean value of a plurality of sets of first blood pressure information which are calculated during the first time period, as the typical value of the first blood pressure information, and a mean value of a plurality of sets of second blood pressure information which are calculated during the second time period, as the typical value of the second blood pressure information.

In the disclosed blood pressure correction information generating device, the device further includes a record controller which records blood pressure information that is calculated by the blood pressure information calculating section after the change time period, and the blood pressure correction information which is generated by the blood pressure correction information generating section, on a recording medium while associating with each other, and the blood pressure correction information generating section generates blood pressure correction information for correcting blood pressure information which is calculated after the change time period, based on: past blood pressure correction information which is associated with blood pressure information that is recorded on the recording medium, and that is calculated before the change time period; and the differential.

In the disclosed blood pressure correction information generating device, the blood pressure correction information generating section generates blood pressure correction information for correcting blood pressure information which is calculated after the change time period, based on a magnitude relationship of the typical value of the first blood pressure information and the typical value of the second blood pressure information, by adding an absolute value of the differential to the past blood pressure correction information which is recorded while associated with blood pressure information that is calculated by the blood pressure information calculating section during the first time period, or by subtracting the absolute value of the differential from the past blood pressure correction information.

In the disclosed blood pressure correction information generating device, when the typical value of the first blood pressure information is larger than the typical value of the second blood pressure information, the blood pressure correction information generating section generates the blood pressure correction information by adding the absolute value of the differential to the past blood pressure correction information which is recorded while associated with the blood pressure information that is calculated by the blood pressure information calculating section during the first time period, and, when the typical value of the first blood pressure information is smaller than the typical value of the second blood pressure information, the blood pressure correction information generating section generates the blood pressure correction information by subtracting the absolute value of the differential from the past blood pressure correction information which is recorded while associated with the blood pressure information that is calculated by the blood pressure information calculating section during the first time period.

In the disclosed blood pressure correction information generating device, the blood pressure correction information generating section converts a difference between a position of the wrist based on the information at start of the change time period which is detected by the wrist position change time period detecting section, and a position of the wrist based on the information at end of the change time period, to a change amount of the blood pressure information, and, in a case where a difference between the change amount and the differential is larger than a predetermined value, stops generation of the blood pressure correction information.

The disclosed blood pressure measurement device includes: a pulse wave detecting section which detects a pulse wave from a wrist of a person to be measured; a blood pressure information calculating section which calculates blood pressure information every pulse or every plurality of pulses based on the pulse wave detected by the pulse wave detecting section; a motion detecting section which outputs motion information according to motion of the wrist; and the blood pressure correction information generating device.

The disclosed blood pressure correction information generating method includes: a wrist position change time period detecting step of detecting a change time period when a position in a gravity direction of a wrist of a person to be measured is changed at a degree equal to or greater than a threshold, based on information that is output from a motion detecting section, the information according to a motion of the wrist of the person to be measured to whom a blood pressure measurement device is attached, the blood pressure measurement device including: a pulse wave detecting section which detects a pulse wave from the wrist of the person to be measured; and a blood pressure information calculating section which calculates blood pressure information every pulse or every plurality of pulses based on the pulse wave detected by the pulse wave detecting section; and a blood pressure correction information generating step of generating blood pressure correction information for correcting the blood pressure information which is calculated by the blood pressure information calculating section after the change time period detected in the wrist position change time period detecting step, based on first blood pressure information which is calculated in the blood pressure information calculating section before the change time period, and second blood pressure information which is calculated by the blood pressure information calculating section, and which is after the change time period.

The disclosed blood pressure correction information generating program causes a computer to execute: a wrist position change time period detecting step of determining a change time period when a position in a gravity direction of a wrist of a person to be measured is changed at a degree equal to or greater than a threshold, based on information that is output from a motion detecting section, the information corresponding to a motion of the wrist of the person to be measured to whom a blood pressure measurement device is attached, the blood pressure measurement device including: a pulse wave detecting section which detects a pulse wave from the wrist of the person to be measured; and a blood pressure information calculating section which calculates blood pressure information every pulse or every plurality of pulses based on the pulse wave detected by the pulse wave detecting section; and a blood pressure correction information generating step of generating blood pressure correction information for correcting the blood pressure information which is calculated in the blood pressure information calculating step after the change time period, based on first blood pressure information which is calculated in the blood pressure information calculating section before the change time period detected by wrist position change time period detecting step, and second blood pressure information which is calculated by the blood pressure information calculating section after the change time period.

According to the invention, it is possible to provide a blood pressure correction information generating device that generates information with which a measurement error in blood pressure information that is caused by a position change of the wrist in a wrist-wear blood pressure measurement device can be correctly corrected, a blood pressure measurement device including the blood pressure correction information generating device, and a blood pressure correction information generating method.

The invention enables accurate measurement to be performed, and therefore can be used in a medical institution.

Although the invention has been described with reference to the specific embodiment, the invention is not limited to the embodiment, and various changes can be made without departing from the technical spirit of the disclosed invention.

What is claimed is:

1. A pressure correction information generating device which, from a recording medium on which blood pressure information that is calculated every pulse or every plurality of pulses based on a pulse wave detected from a wrist of a person to be measured, motion detection information that detects motion of the wrist, and detection time information indicating a time when the motion detection information is detected are recorded in association with one another, reads the blood pressure information, the motion detection information, and the detection time information, and which generates blood pressure correction information for correcting the blood pressure information, the pressure correction information generating device comprising:
   a wrist position change time period detecting section which detects a change time period when a position in a gravity direction of the wrist is changed at a degree equal to or greater than a threshold, based on the motion detection information and the detection time information;
   a blood pressure correction information generating section which generates blood pressure correction information for correcting blood pressure information which is calculated from a pulse wave detected after the change time period, based on first blood pressure information which is calculated from a pulse wave detected during a first time period that is before the change time period detected by the wrist position change time period detecting section, and second blood pressure information which is calculated from a pulse wave detected during a second time period that is after the change time period; and
   a record controller which records the blood pressure correction information that is generated by the blood pressure correction information generating section, on the recording medium while associating with the blood pressure information that is corrected by the blood pressure correction information, wherein
   the blood pressure correction information generating section obtains a differential between a first value of the first blood pressure information and a second value of the second blood pressure information, and, based on a magnitude relationship of the first value of the first blood pressure information and the second value of the second blood pressure information, adds an absolute value of the differential to past blood pressure correction information which is recorded while associated with the blood pressure information that is calculated from the pulse wave detected during the first time period, or subtracts the absolute value of the differential from the past blood pressure correction information, to generate the blood pressure correction information of the blood pressure information calculated from the pulse wave that is detected after the change time period.

2. The pressure correction information generating device according to claim 1, wherein
   the first time period is a time period when dispersion of the blood pressure information calculated from the pulse wave is equal to or smaller than a threshold, and
   the second time period is a time period when dispersion of the blood pressure information calculated from the pulse wave is equal to or smaller than the threshold.

3. The pressure correction information generating device according to claim 1, wherein
   the blood pressure correction information generating section calculates the differential while setting a mean value of a plurality of sets of first blood pressure information which are calculated during the first time period, as the first value of the first blood pressure information, and a mean value of a plurality of sets of second blood pressure information which are calculated during the second time period, as the second value of the second blood pressure information.

4. The pressure correction information generating device according to claim 1, wherein,
   when the first value of the first blood pressure information is larger than the second value of the second blood pressure information, the blood pressure correction information generating section generates the blood pressure correction information by adding the absolute value of the differential to the past blood pressure correction information which is recorded while associated with the blood pressure information that is calculated from the pulse wave detected during the first time period, and,
   when the first value of the first blood pressure information is smaller than the second value of the second blood pressure information, the blood pressure correction information generating section generates the blood pressure correction information by subtracting the absolute value of the differential from the past blood pressure correction information.

5. The pressure correction information generating device according to claim 1, wherein
   the blood pressure correction information generating section converts a difference between a position of the wrist based on the motion detection information at a start of the change time period which is detected by the wrist position change time period detecting section, and a position of the wrist based on the motion detection information at an end of the change time period, to a change amount of the blood pressure information, and, in a case where a difference between the change amount and the differential is larger than a predetermined value, stops generation of the blood pressure correction information.

6. A blood pressure measurement device comprising:
   a pulse wave detector which detects a pulse wave from a wrist of a person to be measured;
   a blood pressure information calculating section which calculates blood pressure information every pulse or every plurality of pulses based on the pulse wave detected by the pulse wave detector;
   a motion detector which outputs motion information according to motion of the wrist; and
   the blood pressure correction information generating device according to claim 1.

7. A blood pressure correction information generating method comprising: from a recording medium on which blood pressure information that is calculated every pulse or every plurality of pulses based on a pulse wave detected from a wrist of a person to be measured, motion detection information that detects motion of the wrist, and detection time information indicating a time when the motion detection information is detected are recorded in association with one another, reading the blood pressure information, the motion detection information, and the detection time information; and generating blood pressure correction information for correcting the blood pressure information, the blood pressure correction information generating method comprising:

determining a change time period when a position in a gravity direction of the wrist is changed at a degree equal to or greater than a threshold, based on the motion detection information and the detection time information;

generating blood pressure correction information for correcting the blood pressure information which is calculated from a pulse wave detected after the change time period, based on first blood pressure information which is calculated from a pulse wave detected during a first time period that is before the change time period detected in the wrist position change time period detecting step, and second blood pressure information which is calculated from a pulse wave detected during a second time period that is after the change time period; and     recording the blood pressure correction information that is generated in the blood pressure correction information generating step, on the recording medium while associating with the blood pressure information that is corrected by the blood pressure correction information, wherein     in generating the blood pressure correction information, a differential between a first value of the first blood pressure information and a second value of the second blood pressure information is obtained, and, in a case where the first value of the first blood pressure information is larger than the second value of the second blood pressure information, an absolute value of the differential is added to past blood pressure correction information which is recorded while associated with the blood pressure information that is calculated from the pulse wave detected during the first time period, to generate the blood pressure correction information, and,     in a case where the first value of the first blood pressure information is smaller than the second value of the second blood pressure information, the absolute value of the differential is subtracted from the past blood pressure correction information, to generate the blood pressure correction information.

8. A non-transitory computer readable medium in which a program causing a computer to execute the blood pressure correction information generating method according to claim 7 is recorded.

\* \* \* \* \*